United States Patent [19]

Argentieri

[11] Patent Number: 4,889,691

[45] Date of Patent: Dec. 26, 1989

[54] MODULAR TISSUE SUPERFUSION CHAMBER

[75] Inventor: Thomas M. Argentieri, 1008 Darby Dr., Yardley, Pa. 19067

[73] Assignee: Thomas Michael Argentieri, Yardley, Pa.

[21] Appl. No.: 215,976

[22] Filed: Jul. 5, 1988

[51] Int. Cl.⁴ .......................... B01L 3/00; C12M 1/34
[52] U.S. Cl. ...................................... 422/102; 422/99; 422/104; 422/68; 435/291
[58] Field of Search ...................... 422/50, 68, 99, 100, 422/102, 104; 436/174, 180; 424/3; 435/1, 283, 289, 291; 128/731, 734; 62/3; 356/244, 246

[56] References Cited

U.S. PATENT DOCUMENTS

| | | | |
|---|---|---|---|
| 4,058,370 | 11/1977 | Suovaniemi | 422/100 |
| 4,066,365 | 1/1978 | Staunton | 356/244 |
| 4,279,860 | 7/1981 | Smolen | 422/100 X |
| 4,395,492 | 7/1983 | Rees | 435/283 |
| 4,629,686 | 12/1986 | Gruenberg | 435/283 X |
| 4,657,868 | 4/1987 | Saxholm | 422/56 X |
| 4,745,759 | 5/1988 | Bauer et al. | 435/1 X |

OTHER PUBLICATIONS

Minnema et al., J. of Neuroscience Methods, "A Superfusion Apparatus for the Examination of Neurotransmitter Release from Synaptosomes", 14: 193–206, (1985).

Primary Examiner—Michael S. Marcus
Assistant Examiner—Rebekah A. Griffith
Attorney, Agent, or Firm—Elizabeth A. Bellamy; John R. Moses; I. William Millen

[57] ABSTRACT

A modular tissue superfusion chamber includes a receptacle support having a recess therein for receiving one of a plurality of modular bath containers which hold tissue samples being tested for electrophysiological responses to compounds. The receptacle support has a Peltier heater therein and is mounted on a magnetic base with a plurality of pillars.

15 Claims, 3 Drawing Sheets

MODULAR TISSUE SUPERFUSION CHAMBER

BACKGROUND OF THE INVENTION

The instant invention relates to chambers for conducting experiments on tissue samples, and more particularly, to apparatus useful in performing procedures such as electrophysiological recordings of cellular activities.

In the pharmaceutical industry, electrophysiological testing of tissue is becoming a widely used in vitro procedure for testing the effects of various compounds on tissue. For example, it is necessary to know whether or not new compounds have electrophysiological activity in heart tissues. Frequently, the tissue samples used in the tests are of different sizes and configurations requiring baths of various sizes and configurations to accommodate the tissue samples. Currently available apparatus for electrophysiological testing does not provide for utilizing the same basic apparatus for tissues of different sizes and configurations. This requires that a separate device be utilized for each tissue sample resulting in increased expense, lab clutter and the need to calibrate and adjust a multiplicity of instruments.

SUMMARY OF THE INVENTION

In view of the afore-discussed need and other needs, it is an object of the instant invention to provide new and improved apparatus for performing experiments requiring cellular electrophysiological recordings.

Upon further study of the specification and appended claims, further objects and advantages of this invention will become apparent to those skilled in the art.

In view of this object and other objects, the instant invention contemplates a tissue superfusion chamber comprising a support chamber having the temperature controller therein and a recess therein in communication with the temperature controller so that the temperature controller readily controls the temperature of whatever element is placed in the recess. The recess has a predetermined size and configuration which matches the external size and configuration of a plurality of modular chambers each having a space therein for containing a tissue sample. The spaces in the modular chambers are of various sizes and configurations so as to accommodate tissue samples of various sizes and configurations and baths of various volumes. Each modular chamber has ports therein for introducing at least one tube and at least one electrode.

The support chamber is preferably mounted by isolation pillars on a magnetic base which firmly mounts the apparatus on a table such as a metal lab table.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
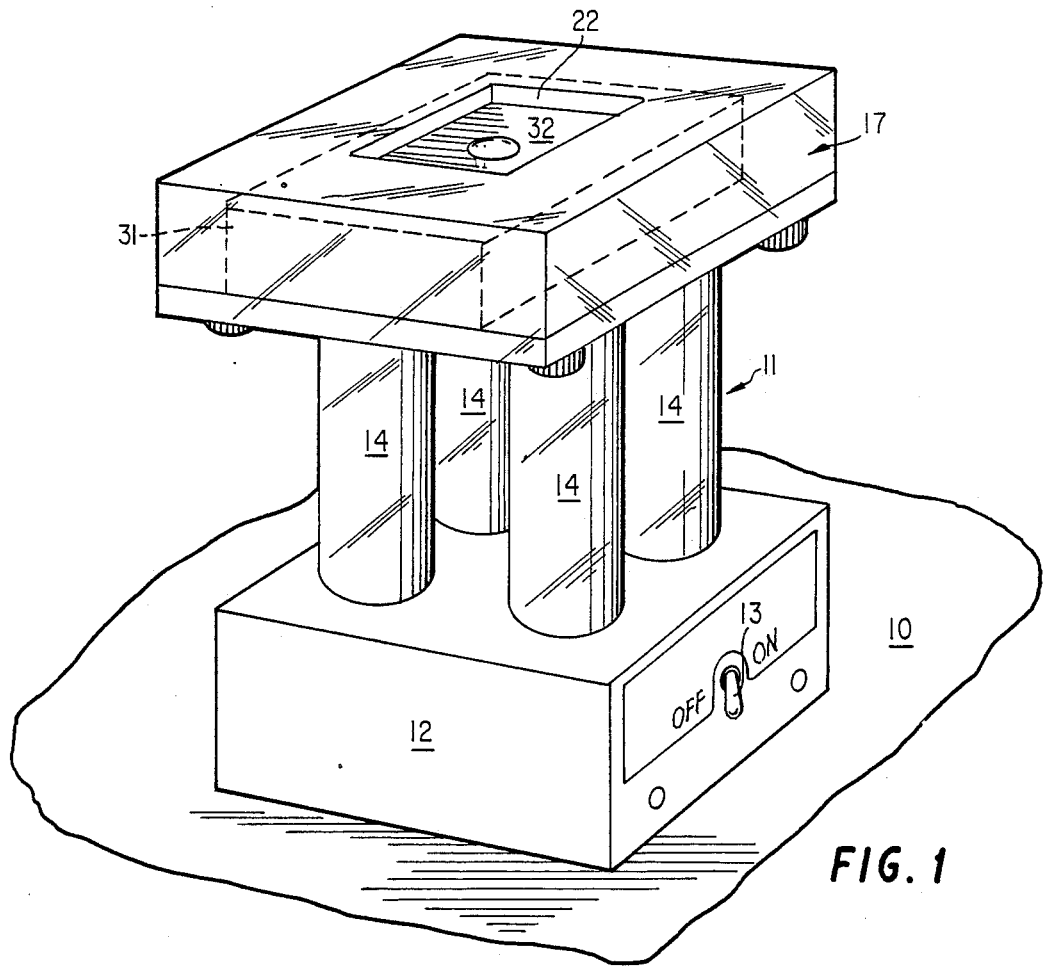
FIG. 1 is a perspective view of the apparatus in accordance with the instant invention showing a support chamber having a recess therein for receiving the modular bath containers of FIGS. 2 and 3.

Referring now to FIG. 1, there is shown the surface 10 of a steel lab table on which the apparatus, designated generally by the numeral 11, of the instant invention is secured by a magnetic base 12. The magnetic base 12 is preferably a low profile base such as the model 150 sold by the Newport Research Corporation which has a height of approximately 1¾ inches and is approximately 4 inches in length and width. The magnetic base has an "on" and "off" switch 3 which allows one to rapidly secure and release the support apparatus 11 to and from the lab table 10.

Figure 7:
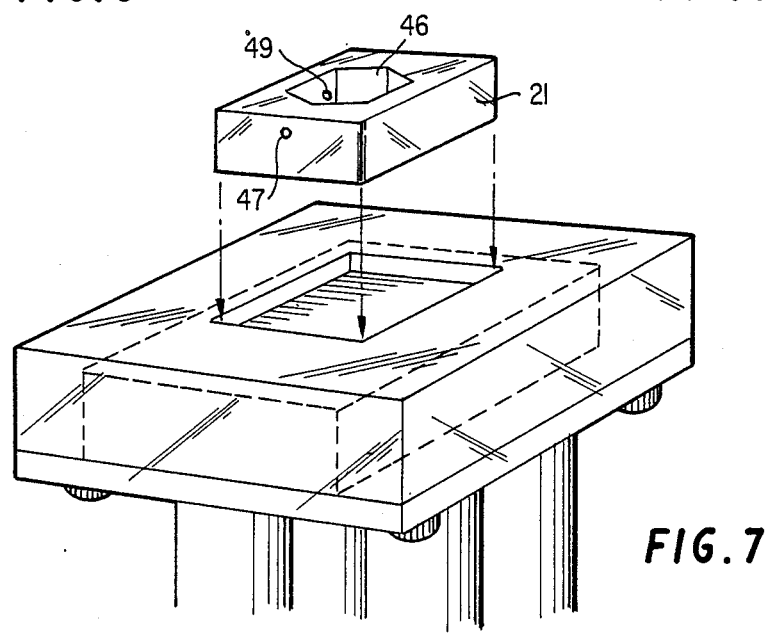
FIG. 7 is a perspective view showing how either one of the modular bath containers is received by the support chamber of FIGS. 1 and 4.

Extending vertically from the support apparatus 12 and secured thereto by mounting screws 113 (FIG. 9) are four pillars 14 each of which are approximately 1 inch in diameter and 4 inches tall. Secured to the top of the pillars 14 by screws 16 (see FIG. 9) is a support chamber, designated generally by the numeral 17, which support chamber supports the modular bath containers of FIGS. 2 and 3, designated generally by the numerals 20 and 21, respectively, in a top recess 22 located in the top of the support chamber as is seen in FIGS. 4, 7 and 9.

Figure 4:
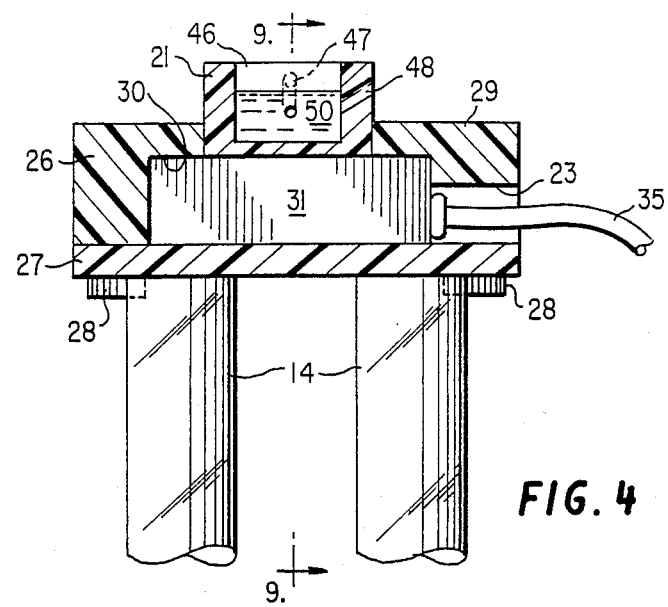
FIG. 4 is a side view partially in section of the support chamber of FIG. 1 shown with the modular bath container of FIG. 3 mounted therein.
Figure 6:
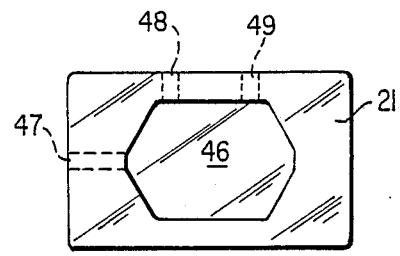
FIG. 6 is a top view of the modular bath container of FIG. 3.
Figure 9:
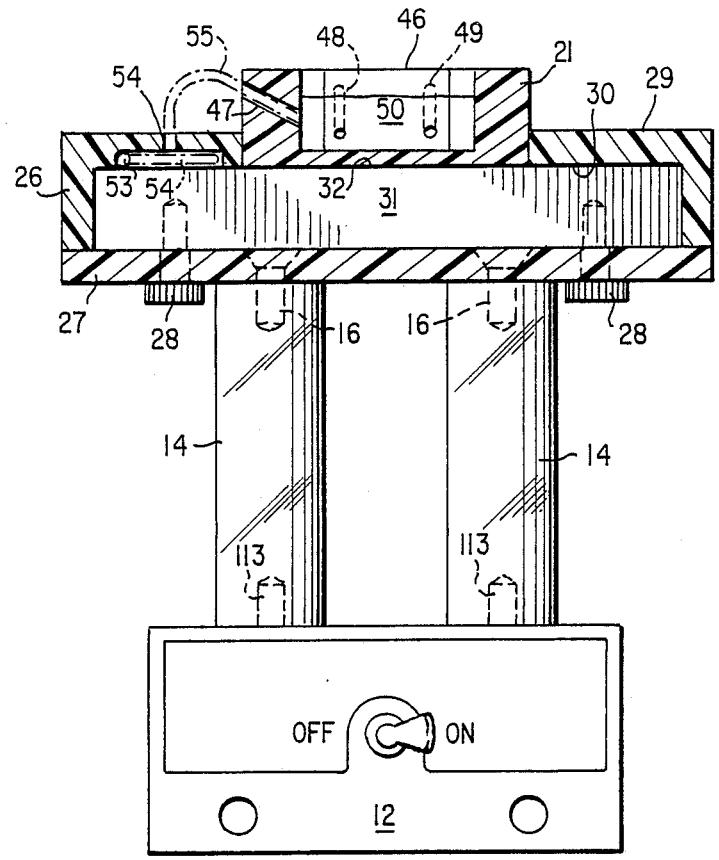
FIG. 9 is a side view partially in section taken along lines 9—9 of FIG. 4.

As is best seen in cross-sectional FIGS. 4 and 9, the support chamber 17 has a receptacle portion 26 and a bottom plate 27 secured to the receptacle portion by four screws 28 to define a chamber 30 therein which communicates with a back recess 23. The recess 22 is formed through a top plate 29 of the receptacle portion.

Received within the chamber 30 is a Peltier device 31 (available from Cambion/Midland Ross, Cambridge, Mass.) which is used to maintain a precise temperature. The Peltier device 31 is a water-cooled, heating and cooling plate utilized in studies in which the electrophysiological characteristics of cells are observed. The Peltier device includes a surface plate 32 which is exposed through the recess 22 in the top of the receptacle portion 26 of the support chamber 17 (see FIG. 8). A power cord 35 supplying current to heat the Peltier device 31 and fluid inlet and outlet lines 36 and 37 for cooling the Peltier device, if desired, are connected to the Peltier device and extend through the back recess 23 of the receptacle portion 26.

Figure 2:
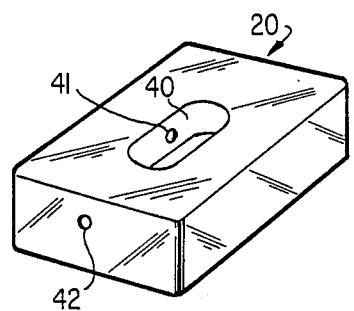
FIG. 2 is a perspective view of a first modular bath container for use with the support chamber of FIG. 1.
Figure 3:
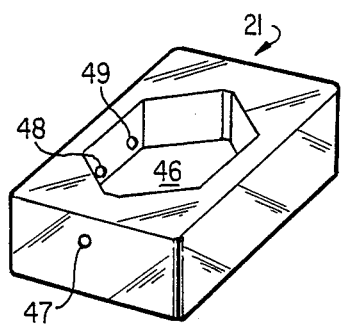
FIG. 3 is a perspective view of a second modular bath container for use with the support chamber of FIG. 1.
Figure 5:
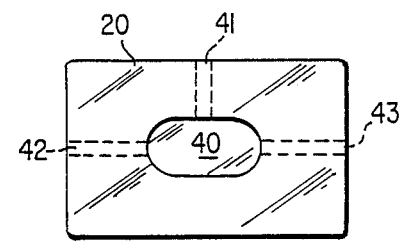
FIG. 5 is a top view of the modular bath container of FIG. 2.

The modular bath containers 20 and 21 shown in FIGS. 2 and 3 have identical exterior peripheral geometries and dimensions so as to be interchangeably fitted into the recess 22 in the receptacle portion 26 of the support chamber 17. Referring now more specifically to the modular bath container 20 shown in FIGS. 2 and 5, it is seen that the container has a relatively small space 40 for containing a pharmacological saline solution bath and tissue sample, which space is oblong in shape and is communicated with by a side port 41 and a pair of end ports 42 and 43. The ports 41, 42 and 43 slope downwardly toward the space 40 so that the external openings of the ports are above the bath within the space 40 (see bath 50 in FIG. 4 for an analogous situation). In this way, conventional tubing and tube electrodes filled with a conductive gel (not shown) can be inserted laterally and longitudinally into the bath through the side and ends of the modular bath 20 to introduce compounds into the bath and to monitor the electrical response of tissue within the bath.

The modular bath 21 which is shown in FIGS. 3, 4, 6, 7 and 9 has a much larger space 46 for containing the pharmacological saline solution bath and tissue sample. Space 46 is six sided and is wider as well as longer than the space 40 of the modular bath container 20. The modular bath container 21 also includes downwardly sloping ports 47, 48 and 49 for receiving tubing and gel containing tubular electrodes to dose and electrically monitor tissue therein. As is seen in FIGS. 4 and 9, the sloping ports 47, 48 and 49 have lower ends beneath the surface of the bath 50 and upper ends above both the surface of the bath and the top surface of the receptacle support 26.

While only two modular bath containers 20 and 21 are shown, it is of course possible to utilize many different modular bath containers with different volumes and configurations for the space containing the bath 50. It is only necessary that the external periphery of whatever modular bath container is being utilized corresponds in size and geometry to the recess 23.

Figure 8:
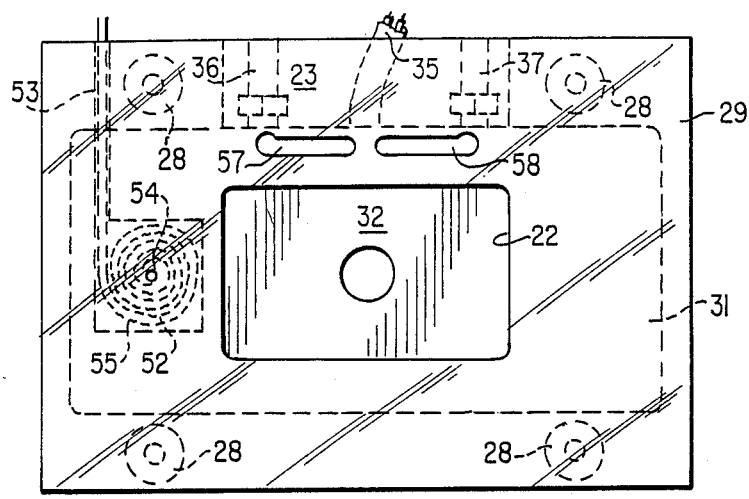
FIG. 8 is a top view of the support chamber of FIG. 1.

Referring now to FIGS. 8 and 9, the top plate 29 of the receptacle support has a square cavity 52 formed therein, which square cavity opens to the top surface 32 of the Peltier device 31. The square cavity 52 has a horizontal groove 53 therein and a vertical bore 54 to accommodate a tube illustrated by dotted lines 55 for carrying fluid to dose the tissue sample within a bath 50. The tube 55 enters through the horizontal groove 53, coils within the square cavity 52, passes through the vertical bore 54 and enters the space 46 containing the bath 50 through sloping bore 47. Fluid flowing through the tube 55 is heated by the Peltier device due to contact therewith while coiled in the square cavity 52. Consequently, the fluid in tube 55 is the same temperature as the bath 50.

As is seen in FIG. 8, the top plate 29 has a pair of grooves or depressions 57 and 58 in the top surface thereof which are filled with a conductive solution. Electrode tubes (not shown) which extend from bath 50 up through bores 48 and 49 are electrically connected to the solution in the grooves 57 and 58 by being inserted therein. Leads having one end in the solution extend from the grooves to electrical monitoring and recording equipment (not shown) used for monitoring the reaction of tissue in the bath 50 to compounds introduced through the tube 55.

In accordance with a constructed embodiment of the invention, the recess 22 in receptacle support 26 is 1½ inch wide, 2½ inches long and ¼ inch deep while the modular bath containers 20 and 21 have slightly smaller dimensions so as to fit relatively snugly within the recess while having a height of about ¾ inch so as to project above the top surface of the support chamber.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A modular tissue superfusion chamber comprising:
   a magnetic base for supporting the chamber on a steel surface;
   support means;
   a support chamber rigidly secured to the support means, the support chamber having a single recess therein of a preselected size and geometry;
   temperature control means disposed in the support chamber and aligned with the recess for precisely controlling heat passing through the recess; and
   a plurality of modular bath containers for interchangeable mounting in the single recess, each having an identical external size and configuration matching that of the recess in the support chamber and each having a space therein of a different size and/or geometry for containing a bath and receiving tissue samples of different sizes and configurations, each modular container having ports therethrough for receiving at least one tube and at least one electrode, which electrode monitors electrophysiological characteristics of the tissue sample immersed in the bath.

2. The modular tissue superfusion chamber of claim 1, wherein the temperature control means is electrically heated and water cooled.

3. The modular tissue chamber of claim 2, wherein the ports in the modular bath containers each slope downwardly from the exterior openings of the containers to the spaces in the containers, wherein the ports are in communication with baths in the containers while having exterior openings above the baths so that the monitoring electrodes and tubing can be inserted into the baths without the bath spilling out of the ports.

4. The modular tissue chamber of claim 3, wherein the support chamber includes a top plate portion, the top plate portion having a cavity therein opening toward the top of the temperature control means, wherein tubing for introducing into the bath substances to be tested is accumulated while in contact with the temperature control means so as to match the temperature of the substance with that of the bath.

5. The modular tissue chamber of claim 4, wherein the top plate of the support chamber has a pair of upwardly facing grooves therein containing a conductive solution; wherein electrodes from the bath have ends in contact with the conductive solution, and wherein leads to electrical monitoring equipment are also inserted into the conductive solution, whereby the conductive solution establishes an electrical connection between the electrodes and the leads.

6. A modular tissue superfusion chamber comprising:
   a magnetic base for supporting the chamber on a steel surface;
   a plurality of support pillars having first and second ends wherein the first ends are secured to the magnetic base;
   a base plate rigidly secured to the second ends of the pillars;
   a support chamber rigidly secured to the base plate, the support chamber including a bottom plate and a receptacle portion rigidly secured to the bottom plate, the receptacle portion and bottom plate cooperating to define a space therebetween, the receptacle having a recess therein of a preselected size and geometry;

temperature control means disposed in the support chamber and aligned with the recess for precisely controlling heat passing through the recess; and a plurality of modular bath containers each having an identical external size and configuration matching that of the recess in the receptacle and each having a space therein of a different size and/or geometry for receiving tissue samples of different sizes and configurations, each modular container having ports therethrough for receiving at least one tube and at least one electrode, which electrodes monitor electrophysiological characteristics of the tissue sample immersed in the bath.

7. The modular tissue superfusion chamber of claim 6, wherein the temperature control means is an electrically heated, water cooled Peltier device.

8. The modular tissue superfusion chamber of claim 7, wherein the recess in the receptacle portion of the support chamber has a height less than the height of the modular bath containers, so that the modular bath containers may be readily inserted into and removed from the recess.

9. The modular tissue chamber of claim 8, wherein the ports, in the modular bath containers each slope downwardly from the exterior openings of the containers to the spaces in the containers, wherein the ports are in communication with baths in the containers while having exterior openings above the baths so that tubes and electrodes can be inserted into the baths without the baths spilling out of the ports.

10. The modular tissue chamber of claim 9, wherein the support chamber includes a top plate portion, the top plate portion having a cavity therein opening toward the top of the Peltier device, wherein tubing for introducing into the bath substances to be tested is coiled while in contact with the Peltier device so as to match the temperature of the substance with that of the bath.

11. The modular tissue chamber of claim 10, wherein the top plate of the support chamber has a pair of upwardly facing grooves therein containing a conductive solution; wherein electrodes from the bath have ends in contact with the conductive solution, and wherein leads to electrical monitoring equipment also are inserted into the conductive solution, whereby the conductive solution establishes an electrical connection between the electrodes and the leads.

12. A modular tissue superfusion chamber comprising:

a magnetic base for supporting the chamber on a steel surface;

support means;

a support chamber rigidly secured to be support means, the support chamber having a recess of a selected depth therein of a preselected size and geometry;

temperature control means, which is electrically heated and water cooled, disposed in the support chamber and aligned with the recess for precisely controlling heat passing through the recess; and a plurality of modular bath containers, each having an identical external size and geometry matching that of the recess in the support chamber, the modular bath containers each having a height greater than the depth of the recess wherein the modular bath containers may be readily inserted into and removed from the recess in the support chamber, each modular bath container having a space therein of a different size and/or geometry for containing a bath and receiving tissue samples of different sizes and configurations, each modular container having ports therethrough for receiving at least one tube and at least one electrode, which electrode monitors electrophysiological characteristics of the tissue sample immersed in the bath.

13. The modular tissue chambers of claim 12, wherein the ports in the modular containers slope downwardly from the exterior openings of the containers to the spaces in the containers, wherein the ports are in communication with baths in the containers while having exterior openings above the baths so that the monitoring electrodes and tubing can be inserted into the baths without the baths spilling out of the ports.

14. The modular tissue chamber of claim 13, wherein the support chamber includes a top plate portion, the top plate portion having a cavity therein opening toward the top of the temperature control means, wherein tubing for introducing into the bath substances to be tested is accumulated while in contact with the temperature control means device so as to match the temperature of the substance with that of the bath.

15. The modular tissue chamber of claim 14, wherein the top plate of the support chamber has a pair of upwardly facing grooves therein containing a conductive solution; wherein electrodes from the bath have ends in contact with the conductive solution, and wherein leads to electrical monitoring equipment are also inserted into the conductive solution, whereby the conductive solution establishes an electrical connection between the electrodes and the leads.

* * * * *